(12) United States Patent
Liu et al.

(10) Patent No.: US 8,309,107 B2
(45) Date of Patent: Nov. 13, 2012

(54) STABLE SOLUTIONS OF ORLISTAT FOR PHARMACEUTICAL DOSAGE FORMS

(75) Inventors: Zhi Liu, Jamestown, NC (US); Dana S. Toops, Parkland, FL (US); Aqeel A. Fatmi, Greensboro, NC (US)

(73) Assignee: Banner Pharmacaps, Inc., High Point, NC (US)

( * ) Notice: Subject to any disclaimer, the term of this patent is extended or adjusted under 35 U.S.C. 154(b) by 243 days.

(21) Appl. No.: 12/574,215

(22) Filed: Oct. 6, 2009

(65) Prior Publication Data

US 2010/0087520 A1  Apr. 8, 2010

Related U.S. Application Data

(60) Provisional application No. 61/103,062, filed on Oct. 6, 2008.

(51) Int. Cl.
*A61K 9/00* (2006.01)
*A61K 9/48* (2006.01)
*A61K 31/365* (2006.01)
*A61K 31/355* (2006.01)
*A61K 31/375* (2006.01)

(52) U.S. Cl. ........ 424/400; 424/408; 424/451; 514/458; 514/449; 514/474

(58) Field of Classification Search ........... 424/400, 424/408, 451; 514/458, 449, 474
See application file for complete search history.

(56) References Cited

U.S. PATENT DOCUMENTS

| | | | |
|---|---|---|---|
| 4,598,089 A | 7/1986 | Hadvary et al. | |
| 5,447,953 A | 9/1995 | Isler et al. | |
| 5,540,917 A | 7/1996 | Isler et al. | |
| 5,716,637 A | 2/1998 | Anselem et al. | |
| 6,004,996 A | 12/1999 | Shah et al. | |
| 6,147,108 A | 11/2000 | Hauptman | |
| 6,358,522 B1 | 3/2002 | Hug et al. | |
| 6,534,539 B2 | 3/2003 | Feinle et al. | |
| 6,703,369 B1 | 3/2004 | de Smidt et al. | |

(Continued)

FOREIGN PATENT DOCUMENTS
EP  1 105 122  4/2005
(Continued)

OTHER PUBLICATIONS

Product Information for MIGLYOL® (Sasol German GmbH, Sep. 2004, pp. 1-7).*

(Continued)

*Primary Examiner* — Aradhana Sasan
(74) *Attorney, Agent, or Firm* — Pabst Patent Group LLP

(57) ABSTRACT

Liquid orlistat-containing fill materials suitable for encapsulating in hard or soft capsules are described herein. The fill material contains orlistat dissolved in one or more medium chain triglycerides or medium chain partial triglycerides, one or more citrate esters, and combinations thereof. The fill material can also contain one or more pharmaceutically acceptable excipients. In one embodiment, the fill material is substantially free of surfactants. The fill material can be encapsulated in hard or soft, gelatin or non-gelatin capsules. The capsules may be coated to modify release of orlistat from the capsule. Alternatively, the fill material can be encapsulated in an enteric capsule, wherein the enteric polymer is a component of the capsule shell, rather than a coating over the capsule shell. The fill materials are stable at elevated temperatures over an extended period of time and allow for high loadings of orlistat (e.g., 20% w/w or higher).

24 Claims, 6 Drawing Sheets

U.S. PATENT DOCUMENTS

| | | |
|---|---|---|
| 6,730,319 B2 | 5/2004 | Maeder et al. |
| 6,734,314 B2 | 5/2004 | Keri et al. |
| 2003/0027786 A1 | 2/2003 | Maeder et al. |
| 2004/0175420 A1 | 9/2004 | de Smidt et al. |
| 2005/0101562 A1 | 5/2005 | Maeder et al. |
| 2008/0021092 A1 | 1/2008 | Murpani et al. |

FOREIGN PATENT DOCUMENTS

| | | |
|---|---|---|
| EP | 1 399 152 | 3/2007 |
| EP | 1 399 153 | 10/2007 |
| JP | 2005-126396 * | 5/2005 |
| WO | WO 97/40823 | 11/1997 |
| WO | WO 00/15217 | 3/2000 |
| WO | WO 01/19340 | 3/2001 |
| WO | WO 01/19378 | 3/2001 |
| WO | WO 03/009840 | 2/2003 |
| WO | WO 03/047531 | 6/2003 |
| WO | WO 2004/030658 | 4/2004 |
| WO | WO 2005/026140 | 3/2005 |
| WO | WO 2005/027880 A1 * | 3/2005 |
| WO | WO 2007/039814 | 4/2007 |

OTHER PUBLICATIONS

Kalivianakis, et al., "Validation in an animal model of the carbon 13-labeled mixed triglyceride breath test for the detection of intestinal fat malabsorption," *J. Pediatrics*, 135(4): 444-50 (1999).

Mohammadi et al., "A stability-indicating high performance liquid chromatographic assay for the determination of orlistat in capsules", *J. Chrom. A*, 1116:153-157 (2006).

* cited by examiner

STABLE SOLUTIONS OF ORLISTAT FOR PHARMACEUTICAL DOSAGE FORMS

CROSS-REFERENCE TO RELATED APPLICATIONS

Priority is claimed to U.S. Ser. No. 61/103,062 filed Oct. 6, 2008.

FIELD OF THE INVENTION

This invention is in the field of pharmaceutical compositions, specifically orlistat-containing liquid filled soft or hard capsules.

BACKGROUND OF THE INVENTION

Orlistat (also known as tetrahydrolipstatin (THL) and marketed under the trade name XENICAL ORLISTAT® by Roche; or over-the-counter as ALLI® by GlaxoSmithKline), is a drug designed to treat obesity. Orlistat is the saturated derivative of lipstatin, a potent natural inhibitor of pancreatic lipases isolated from the bacterium *Streptomyces toxytricini*. However, due to simplicity and stability, orlistat, rather than lipstatin, was developed as an anti-obesity drug.

Orlistat prevents the absorption of fats from the human diet, thereby reducing caloric intake. Orlistat works by inhibiting pancreatic lipase, an enzyme that breaks down triglycerides in the intestine. Without this enzyme, triglycerides from the diet are prevented from being hydrolyzed into absorbable free fatty acids and are excreted undigested. Only trace amounts of orlistat are absorbed systemically; the primary effect is local lipase inhibition within the GI tract after an oral dose. The primary route of elimination is through the feces.

The chemical structure of orlistat was originally described in U.S. Pat. No. 4,598,089. Due to its low melting point of about 44° C., orlistat undergoes both hydrolytic and thermal degradation, particularly when stored in a humid atmosphere or above 35° C. in a dry atmosphere. XENICAL ORLISTAT® and ALLI® are sold as granule-filled hard shell capsules. XENICAL ORLISTAT® and ALLI® contain orlistat granulated with microcrystalline cellulose, sodium starch glycolate, sodium lauryl sulfate, povidone and talc. However, solid dosage forms, such as tablets, or dosage forms containing solid fill materials, such as hard gelatin capsules, can be difficult to formulate from a powder mix or by conventional wet granulation methods due to picking and sticking phenomena during tablet compression or encapsulation. Further, granulated or crystalline orlistat is subject to thermal and hydrolytic degradation during both manufacturing and subsequent storage as described above.

In an effort to overcome these difficulties, U.S. Pat. No. 6,004,996 to Shah et al. describes dosage forms containing orlistat-containing particles or pellets having a diameter from 0.25 mm to 2 mm, preferably from 0.5 to 1.5 mm, and a stabilizer. The pellets also preferably contain microcrystalline cellulose. The pellets can be encapsulated in gelatin capsules. Shah alleges that the products are chemically stable; however, Shah provides no data to support this conclusion. Further, all of the pellets are dried at temperatures less than 35° C., which is the temperature above which orlistat begins to degrade. Shah does not disclose or suggest solutions containing orlistat encapsulated in capsules nor does Shah disclose any data related to the dissolution profiles of the formulations.

In addition to the stability problems associated with solid orlistat formulations, administration of orlistat causes several side effects, one of the more severe being oil spotting. This phenomenon reflects the physical separation of liquid unabsorbed dietary fiber from the bulk solids in the lower large intestine. Reformulations of orlistat have been explored in an attempt to alleviate oil spotting. For example, U.S. Pat. No. 6,703,369 to de Smidt et al. describes compositions containing orlistat and at least one fatty acid ester of a polyol, wherein the fatty acid ester has a melting point greater than 37° C. A preferred fatty acid ester of a polyol is a glyceride ester. The mixture of the fatty acid of a polyol and orlistat are co-melted, additional excipients, if any, are added, and the mixture is stirred and cooled until solidification. The solid material is ground and the resulting solid particles are pressed into a tablet or encapsulated in hard shell capsules.

European Patent No. EP 1 399 152 to F. Hoffman-La Roche AG describes compositions containing a lipase inhibitor, preferably orlistat, and a sucrose fatty acids ester, such as a mono-, d-, tri-, or tetraester. The mixture of the lipase inhibitor and the sucrose fatty acid ester is a solid material as shown in the examples, not a solution. For example, Example 9 describes encapsulating pellets containing orlistat and sucrose palmitate in gelatin capsules.

European Patent No. EP 1 399 153 to F. Hoffman-La Roche AG describes compositions containing orlistat and a fatty acid or fatty acid salt or mixtures thereof. The compositions described in the '153 patent are solids at the time of manufacture, not solutions.

European Patent No. EP 1 105 122 to F. Hoffman-La Roche AG describes compositions containing a lipase inhibitor and one or more additives, such as poorly digestible, poorly fermentable, hydrophilic and/or hydrocolloidal food grade thickeners and emulsifiers. The compositions described in the '122 patent are solids at the time of manufacture, not solutions, and are reconstituted to form suspensions (see Example 1).

The art discussed above disclose solid orlistat formulations. As discussed above, it is known in the art that crystalline and granulated orlistat is susceptible to thermal and hydrolytic degradation, particularly at elevated temperatures (e.g., above 35° C.). The art does not provide any data regarding the chemical and/or physical stability of the various solid formulations.

U.S. Patent Application Publication No. 2004/0175420 to de Smidt et al. describes compositions containing at least one lipase inhibitor, such as orlistat, at least one surfactant, and at least one dispersant. Most of the examples in the '420 application describe a solid fill material. Examples 6 and 7 describe what appear to be liquid fills; however, the carriers are polyethylene glycol, glycerol, and polyethylene glycol 40 stearate. As shown in the examples below, formulations containing orlistat dissolved in a mixture of polyethylene glycol 400 and polyethylene glycol 600 solidify upon cooling to form a white solid. Also, polyethylene glycol is incompatible with orlistat, accelerating degradation of the active agent. The '420 application does not disclose or suggest fill materials containing orlistat dissolved in medium chain triglycerides, citrate esters, or combinations thereof. The '420 application does not disclose any data related to the stability of the formulations and/or the release profile of the formulations.

There exists a need for lipase inhibitor-containing fill materials, particularly orlistat-containing liquid fill materials, which are chemically and physically stable over an extended period of time.

Therefore, it is an object of the invention to provide orlistat-containing liquid fill materials which are chemically and physically stable over an extended period of time, and methods of making and using thereof.

It is further an object of the invention to provide orilstat-containing liquid fill materials having a high loading of orlistat, which can reduce the size of the capsule needed and thus improve patient compliance, and methods of making and using thereof.

It is still further an object of the invention to provide orlistat-containing liquid fill materials, in the form of clear solutions, which can be encapsulated in clear, transparent capsules.

SUMMARY OF THE INVENTION

Liquid lipase inhibitor-containing fill materials suitable for encapsulating in hard or soft capsules are described herein. The preferred lipase inhibitor is orlistat. The fill material contains orlistat dissolved in one or more medium chain triglycerides or medium chain partial triglycerides, one or more citrate esters, and combinations thereof. Suitable medium chain triglycerides include, but are not limited to, $C_2$-$C_{10}$ medium chain triglycerides such as those available from Abitec Corp., Columbus, Ohio, under the tradename Captex® (e.g., Captex® 355); medium chain partial triglycerides, such as those available from Sasol Limited under the tradename Imwitor®; Miglyol® 812, Neobee® M-5, and combinations thereof. Suitable citrate esters include, but are not limited to, acetyltri-n-butyl citrate, acetyltriethyl citrate, tri-n-butyl citrate, triethyl citrate, acetyltri-n-hexyl citrate, n-butylryltri-n-hexyl citrate and combinations thereof.

Liquid fill materials can have several advantages over solid fill materials. For example, liquid fills can be encapsulated at about room temperature, while solid fill materials generally have to be encapsulated at elevated temperatures, which can result in degradation of the thermally liable orlistat. Transparent, liquid fills can be used to manufacture clear soft gel capsules which are appealing to consumers because clear, transparent softgel capsules may convey the image of high purity and high quality.

The fill material can also contain one or more pharmaceutically acceptable excipients, such as plasticizers, crystallization inhibitors, bulk filling agents, solubilizers, bioavailability enhancers, additional solvents, pH-adjusting agents, surfactants, antioxidants, preservatives, and combinations thereof. In one embodiment, the fill material is substantially free of surfactants, which is advantageous since it lowers the manufacturing costs of the product. Further, several types of surfactants are known to be incompatible with orlistat. For example, dissolving or dispersing orlistat in polyethylene glycol can accelerate degradation of the active agent. Chremophor® EL emulsifying agent was also found to accelerate degradation of orlistat, likely due to the polyethylene glycol moiety. Other common surfactants, such as polysorbates, which contain a polyethylene glycol moiety can cause phase separation and/or accelerate degradation of the orlistat. Other surfactants, such as Span 80, were observed to cause phase separation in various orlistat solutions.

The fill material can be encapsulated in hard or soft, gelatin or non-gelatin capsules. The capsules may be coated to target release of orlistat from the dosage form at a particular location in the gastrointestinal tract. Alternatively, the fill material can be encapsulated in an enteric capsule, wherein the enteric polymer is a component of the capsule shell, rather than a coating over the capsule shell.

Soft or hard capsules containing the liquid fill materials described herein are suitable for the control or prevention of obesity and hyperlipaemia. The fill materials are chemically (e.g., little or no degradation of orlistat in the fill material) and physically (e.g., little or no precipitation of orlistat from the fill solution) stable at elevated temperatures over an extended period of time. The use of liquid fills eliminates orlistat phase transition, such as precipitation, experienced in the current commercially available solid dosage forms, which is associated with destabilization of the dosage form. The liquid fill solutions allow for high loadings of orlistat (e.g., 20% w/w or higher) compared to solid formulations, which allows for the use of smaller softgel capsules to deliver the required dose and thereby improve patient compliance.

BRIEF DESCRIPTION OF THE DRAWINGS

FIG. 1A shows the percent degradation of orlistat as a function of time (days) at 65° C. for orlistat alone (◇), orlistat dissolved in PEG400 (□), orlistat dissolved in PEG400 and butylated hydroxyanisole (BHA) (△), orlistat dissolved in PEG400 and Span 80 (○), orlistat dissolved in Captex 355 (●), and orlistat dissolved in Captex 355 and BHA (◆). FIG. 1B is a graph showing the percent degradation of orlistat as a function of time (days) at 65° C. for orlistat alone (◇) and orlistat dissolved in triethyl citrate (TEC) and BHA.

DETAILED DESCRIPTION OF THE INVENTION

I. Definitions

Figure 1A:
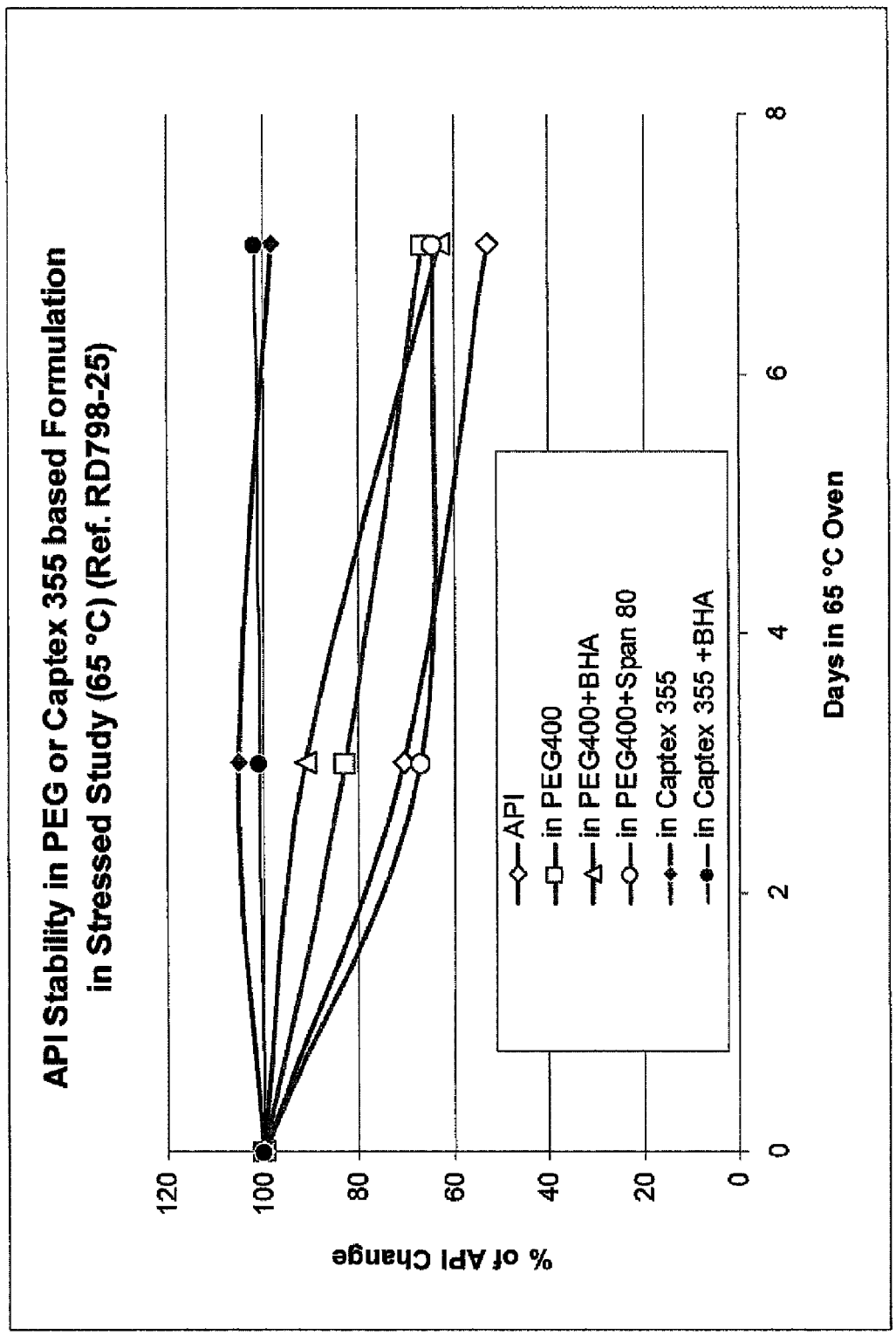
FIGS. 1A and 1B are graphs showing percent degradation of orlistat as a function of time (days) at 65° C.

"Medium chain triglycerides", as used herein, refers to $C_2$-$C_{12}$ triglycerides or $C_2$-$C_{12}$ partial triglycerides. Preferred medium chain triglycerides are typically liquid at room temperature and processing temperatures, for example, from about 25° C. to about −5° C. (see Handbook of Pharmaceutical Excipients, 4th Edition, Edit by R C Rowe, P J Sheskey, and P J Weller, Pharmaceutical Press 2003, London & Chicago, page 378 to 380). Preferred medium-chain triglycerides are liquids at temperatures above −5° C.

"Citric acid esters", "esters of citric acid", and "citrate esters" as used interchangeable and refer to compounds having the formula shown below:

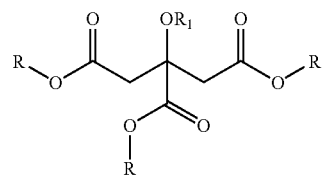

wherein R is a linear, branched, or cyclic $C_{1-30}$, preferably $C_{1-10}$, alkyl group and $R_1$ is a hydrogen or an acyl group. In one embodiment, R is a methyl, ethyl, propyl, or butyl and $R_1$ is hydrogen or an acetyl group. The citrate esters are preferably liquids at room temperature and processing temperatures, for example, from about 25° C. or higher to about −45° C.

"Substantially free of a surfactant", as used herein, refers to a formulation that contains no surfactant or only trace amounts of surfactants, for example less than 1%, preferably less than 0.5%, most preferably less than 0.1%. Formulations that were substantially free of surfactant showed minimal active agent degradation. Minimal degradation, as used herein, means less than 10%, preferably less than 5%, more preferably less than 3%, and most preferably less than 1% of the orlistat is lost after storage at 40° C. and 75% relative humidity for a period of three months. Orlistat can be lost by precipitation of the orlistat from solution, chemical degradation of orlistat itself, or both. Minimal degradation amounts may differ for different carriers (e.g., Captex 355 vs. triethylcitrate) due to the difference in the chemical and physical properties of the carriers.

"High apparent solubility" and "high loading" are used interchangeably and refer to high concentration of orlistat dissolved in a solvent or carrier (expressed as weight/weight (w/w) or weight/volume (w/v)). Fill materials having a high loading of orlistat are stable, i.e., do not phase separate or precipitate under typical storage conditions, e.g., 40° C. at 75% relative humidity for a period of at least seven days, preferably at least 30 days, more preferably at least 90 days.

II. Capsules

A. Fill Material

Liquid lipase inhibitor-containing fill materials suitable for encapsulating in hard or soft capsules are described herein. In a preferred embodiment, the lipase inhibitor is orlistat. The fill material contains orlistat dissolved in one or more medium chain triglycerides or medium chain partial triglycerides, one or more citrate esters, and combinations thereof. The liquid fill materials described herein are stable at elevated temperatures over an extended period of time. The fill materials allow for high loadings of orlistat, for example, up to 45% by weight or higher, preferably from about 20% w/w to about 30% by weight, provided that the fill remain a liquid when cooled to room temperature. The liquid fills may be heated (e.g., to 40 to 45° C.) to facilitate dissolution of higher concentrations of orlistat provided that the fills remain liquid upon cooling.

1. Lipase Inhibitors

The fill material contains one or more lipase inhibitors. Exemplary lipase inhibitors include, but are not limited to, the compounds described in U.S. Pat. No. 4,598,089 to Hadvary et al. The lipase inhibitors can be used for the control or prevention of obesity and hyperlipaemia.

In one embodiment, the lipase inhibitor is orlistat. Orlistat is formed by the hydrogenation of lipstatin. Lipstatin is produced by the cultivation of the microorganism *Streptomyces toxytricini*. The structure of orlistat is shown below:

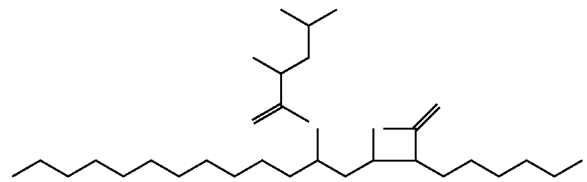

Due to its low melting point of about 44° C., orlistat undergoes both hydrolytic and thermal degradation, particularly when stored in a humid atmosphere or above 35° C. in a dry atmosphere. The fill materials described herein are solutions, wherein orlistat is dissolved in the carrier. Highly mobile physical states, such as liquids, typically exhibit increased bioavailability compared to solid formulations. Further, the absence of crystalline or granulated orlistat avoids the stability problems associated with solid orlistat as shown in the examples.

2. Solvents

The fill material contains one or more solvents selected from medium chain triglycerides or partial triglycerides, citric acid esters, and combinations thereof. The fill material remains a liquid after dissolution of orlistat and encapsulation of the fill in capsules.

i. Medium Chain Triglycerides

In one embodiment, the carrier is one or more medium chain triglycerides, one or medium chain partial triglyerides, or combinations thereof. Medium chain triglycerides (MCTs) are medium-chain, preferably 2 to 12 carbon, more preferably 8-10 carbon, fatty acid esters of glycerol. The names of the medium chain fatty acids (and the corresponding number of carbons) found in MCTs are: butyric (C4), valeric (C5), caproic (C6), caprylic (C8), pelargonic (C9), capric (C10) and lauric acid (C12). Suitable medium chain fatty acids include, but are not limited to, medium chain triglycerides available from Abitec Corp., Columbus, Ohio, under the tradename Captex®, such as Captex® 355; medium chain partial triglycerides available from Sasol under the tradename Imwitor®; Miglyol 812; Neobee M-5 (available from Stepan Company); and combinations thereof. In one embodiment, the medium chain triglyceride is Captex® 355, which is manufactured by the esterification of glycerin and fatty acids (mainly caprylic acid and capric acid) which originate from coconut and/or palm kernel vegetable sources. The concentration of the medium chain triglycerides is from about 45% to about 95% by weight of the composition, more preferably from about 60% to about 95% by weight of the composition, most preferably from about 70% to about 95% by weight of the composition. The preferred medium chain triglycerides are clear liquids at room temperature. This allows for the manufacture of colorless, transparent liquid fill materials which can be encapsulated in transparent softgel capsules.

Fill materials prepared from MCTs have a percent orlistat loading from about 5% to about 45% by weight, preferably from about 5% to about 30% by weight, more preferably from about 5% to about 20% by weight. Fill materials containing orlistat dissolved in Captex 355, alone or in combination with a citrate ester, are stable, showing little or no drug degradation and/or phase separation when stored at 65° C. for a period of 7 days, even absent secondary stabilizers such as butylated hydroxyanisole (BHA).

ii. Citrate Esters

In another embodiment, the carrier is a citrate ester. Suitable citrate esters include, but are not limited to, acetyltri-n-butyl citrate (ATBC), acetyltriethyl citrate (ATEC), tri-n-butyl citrate (TBC), triethyl citrate (TEC), acetyltri-n-hexyl citrate (ATHC), n-butylryltri-n-hexyl citrate (BTHC) and combinations thereof. In one embodiment, the citrate ester is triethyl citrate. Citric acid esters are sold under the tradename Citroflex® and are available from Morflex, Inc., Greensboro, N.C. The preferred citrate esters are also typically clear liquids at room temperature. This allows for the manufacture of colorless, transparent liquid fill materials which can be encapsulated in transparent softgel capsules. In contrast, current commercial orlistat formulations (e.g., XENICAL ORLISTAT® and ALLI®), and formulations prepared using polyethylene glycol as the solvent, are solid fill materials encapsulated in a capsule. The solid fill results in a capsule that is opaque, which may be less aesthetically-pleasing to consumers. The concentration of the citrate ester(s) is from about 45% to about 95% by weight of the composition, more preferably from about 60% to about 95% by weight of the composition, most preferably from about 70% to about 95% by weight of the composition.

Liquid fill materials prepared from citrate esters have a percent orlistat loading from 5% to about 45% by weight, preferably from about 5% to about 30% by weight, more preferably from about 5% to about 20% by weight. Fill materials containing orlistat dissolved in triethyl citrate, alone or in combination with an anti-oxidant, are stable, showing little or no drug degradation and/or phase separation when stored at 65° C. for a period of 7 days.

3. Fill Additives

The fill material may also contain one or more pharmaceutically acceptable additives or excipients that are considered safe and effective and may be administered to an individual without causing undesirable biological side effects or unwanted interactions. Suitable fill additives include, but are not limited to, plasticizers, crystallization inhibitors, bulk filling agents, solubilizers, bioavailability enhancers, additional solvents, pH-adjusting agents, surfactants, anti-oxidants, preservatives, and combinations thereof.

In one embodiment, the fill material is substantially free of surfactant. The examples demonstrate that fill materials containing orlistat dissolved in medium chain triglycerides (MCTs), citrate esters, or combinations thereof, and substantially free of surfactant, exhibit dissolution profiles equivalent to the commercially available orlistat formulations, XENICAL® and ALLI®.

In another embodiment, the fill material further contains a stabilizer, such as an antioxidant. Suitable antioxidants include, but are not limited to, butylated hydroxyanisole (BHA); ascorbic acid, its salts and esters; Vitamin E, tocopherol and its salts; sodium metabisulphite; propyl gallate; and butylated hydroxytoluene (BHT). In some embodiments, the stability of the formulation was essentially the same with and without a stabilizer.

B. Capsule Shell

The capsule shells are prepared using film forming polymers. Suitable film forming polymers include natural polymers, such as gelatin, and synthetic film forming polymers, such as modified celluloses. Suitable modified celluloses include, but are not limited to, hydroxypropyl methyl cellulose, methyl cellulose, hydroxypropyl methyl cellulose acetate succinate, hydroxypropyl methyl cellulose phthalate, and cellulose acetate phthalate. Hard or soft capsules can be used to administer orlistat. Hard shell capsule are typically prepared by forming the two capsule halves, filling one of the halves with the fill solution, and then sealing the capsule halves together to form the finished capsule. Soft gelatin capsules are typically prepared using a rotary die encapsulation process as described below.

1. Gelatin Capsules

Gelatin is the product of the partial hydrolysis of collagen. Gelatin is classified as either Type A or Type B gelatin. Type A gelatin is derived from the acid hydrolysis of collagen while Type B gelatin is derived from the alkaline hydrolysis of collagen. Traditionally, bovine bones and skins have been used as raw materials for manufacturing Type A and Type B gelatin while porcine skins have been used extensively for manufacturing Type A gelatin. In general, acid-processed gelatins form stronger gels than lime-processed gelatins of the same average molecular weight. The capsules can be formulated as hard or soft gelatin capsules.

2. Non-Gelatin Capsules i. Non Gelatin Shell

Capsules can be prepared from non-gelatin materials, such as carrageenan or modified celluloses. Carrageenan is a natural polysaccharide hydrocolloid, which is derived from seaweed. It includes a linear carbohydrate polymer of repeating sugar units, without a significant degree of substitution or branching. Most, if not all, of the galactose units on a carrageenan molecule possess a sulfate ester group. There are three main types of carrageenan: cappa, iota and lambda; although minor forms called mu and nu carrageenan also exist.

3. Shell Additives

Suitable shell additives include plasticizers, opacifiers, colorants, humectants, preservatives, flavorings, and buffering salts and acids, and combinations thereof.

Plasticizers are chemical agents added to gelatin to make the material softer and more flexible. Suitable plasticizers include, but are not limited to, glycerin, sorbitol solutions which are mixtures of sorbitol and sorbitan, and other polyhydric alcohols such as propylene glycol and maltitol or combinations thereof.

Opacifiers are used to opacify the capsule shell when the encapsulated active agents are light sensitive. Suitable opacifiers include titanium dioxide, zinc oxide, calcium carbonate and combinations thereof.

Colorants can be used to for marketing and product identification/differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl esters (collectively known as "parabens") or combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to inhibit cross-linking of the gelatin.

C. Enteric Capsules

Alternatively, the liquid fills can be incorporated into an enteric capsule, wherein the enteric polymer is a component of the capsule shell, as described in WO 2004/030658 to Banner Pharmacaps, Inc. The enteric capsule shell is prepared from a gelatin mass comprising a film-forming polymer, an acid-insoluble polymer which is present in an amount making the capsule resistant to the acid within the stomach, an aqueous solvent, and optionally, one or more plasticizers and/or colorants. Other suitable shell additives including opacifiers, colorants, humectants, preservatives, flavorings, and buffering salts and acids may be added.

1. Film-Forming Polymers

Exemplary film-forming polymers can be of natural or synthetic origin. Natural film-forming polymers include gelatin and gelatin-like polymers. Other suitable natural film-forming polymers include shellac, alginates, pectin, and zeins. Synthetic film-forming polymers include hydroxypropyl methyl cellulose, methyl cellulose, hydroxypropyl methyl cellulose acetate succinate, hydroxypropyl methyl cellulose phthalate, cellulose acetate phthalate, and acrylates such as poly(meth)acrylate. The weight ratio of acid-insoluble polymer to film-forming polymer is from about 15% to about 50%. In one embodiment, the film forming polymer is gelatin.

2. Acid-Insoluble Polymers

Exemplary acid-insoluble polymers include cellulose acetate phthalate, cellulose acetate butyrate, hydroxypropyl methyl cellulose phthalate, algenic acid salts such as sodium or potassium alginate, shellac, pectin, acrylic acid-methylacrylic acid copolymers (available under the tradename EUDRAGIT® from Rohm America Inc., Piscataway, N.J. as a powder or a 30% aqueous dispersion; or under the tradename EASTACRYL®, from Eastman Chemical Co., Kingsport, Tenn., as a 30% dispersion). In one embodiment, the acid-insoluble polymer is EUDRAGIT® L100, which is a methacrylic acid/methacrylic acid methyl ester copolymer. The acid-insoluble polymer is present in an amount from about 8% to about 20% by weight of the wet gelatin mass. The weight ratio of acid-insoluble polymer to film-forming polymer is from about 15% to about 50%.

3. Aqueous Solvent

Hard and soft capsules are typically prepared from solutions or suspensions of the film forming polymer and the acid-insoluble polymer.

Suitable solvents include water, aqueous solvents, and organic solvents. In one embodiment, the solvent is water or an aqueous solvent. Exemplary aqueous solvents include water or aqueous solutions of alkalis such as ammonia, sodium hydroxide, potassium hydroxide, ethylene diamine, hydroxylamine, tri-ethanol amine, or hydroalcoholic solutions of the same. The alkali can be adjusted such that the final pH of the gelatin mass is less than or equal to 9.0, preferably less than or equal to 8.5, more preferably less than or equal to 8.0. In one embodiment, the alkali is a volatile alkali such as ammonia or ethylene diamine.

4. Plasticizers

Exemplary plasticizers include glycerol, glycerin, sorbitol, polyethylene glycol, citric acid, citric acid esters such as triethylcitrate, polyalcohols with 3-6 carbons and combinations thereof. The plasticizer to polymer (film forming polymer plus acid-insoluble polymer) ratio is from about 10% to about 50% of the polymer weight.

II. Method of Manufacture

A. Capsule Fill

The fill material is prepared by dissolving orlistat in a solvent selected from medium chain triglycerides or partial triglycerides, citrate esters, and combinations thereof. The triglyceride(s) and/or citrate esters may be heated to facilitate dissolution of the orlistat. Upon cooling to room temperature and encapsulation, the solution remains a liquid. The fill is typically deaerated prior to encapsulation in a soft gelatin capsule.

B. Capsule Shell

1. Gelatin or Non-Gelatin Capsules

The main ingredients of the capsule shell are gelatin (or a gelatin substitute for non-gelatin capsules), plasticizer, and purified water. The primary difference between soft and hard capsules is the amount of plasticizer present in the capsule shell.

Typical gel formulations contain (w/w) 40-50% gelatin, 20-30% plasticizer, and 30-40% purified water. Most of the water is subsequently lost during capsule drying. The ingredients are combined to form a molten gelatin mass using either a cold melt or a hot melt process. The prepared gel masses are transferred to preheated, temperature-controlled, jacketed holding tanks where the gel mass is aged at 50-60° C. until used for encapsulation.

i. Cold Melt Process

The cold melt process involves mixing gelatin with plasticizer and chilled water and then transferring the mixture to a jacket-heated tank. Typically, gelatin is added to the plasticizer at ambient temperature (18-22° C.). The mixture is cooked (57-95° C.) under vacuum for 15-30 minutes to a homogeneous, deaerated gel mass. Additional shell additives can be added to the gel mass at any point during the gel manufacturing process or they may be incorporated into the finished gel mass using a high torque mixer.

ii. Hot Melt Process

The hot melt process involves adding, under mild agitation, the gelatin to a preheated (60-80° C.) mixture of plasticizer and water and stirring the blend until complete melting is achieved. While the hot melt process is faster than the cold melt process, it is less accurately controlled and more susceptible to foaming and dusting.

iii. Soft Capsules

Soft capsules are typically produced using a rotary die encapsulation process. The gel mass is fed either by gravity or through positive displacement pumping to two heated (48-65° C.) metering devices. The metering devices control the flow of gel into cooled (10-18° C.), rotating casting drums. Ribbons are formed as the cast gel masses set on contact with the surface of the drums.

The ribbons are fed through a series of guide rolls and between injection wedges and the capsule-forming dies. A food-grade lubricant oil is applied onto the ribbons to reduce their tackiness and facilitate their transfer. Suitable lubricants include mineral oil, medium chain triglycerides, and soybean oil. Fill formulations are fed into the encapsulation machine by gravity. In the preferred embodiment, the soft capsules contain printing on the surface, optionally identifying the encapsulated agent and/or dosage.

C. Enteric Capsules

A method of making an enteric capsule shell is described in WO 2004/030658 to Banner Pharmacaps, Inc. The enteric mass is typically manufactured by preparing an aqueous solution comprising a film-forming, water soluble polymer and an acid-insoluble polymer and mixing the solution with one or more appropriate plasticizers to form a gelatin mass. Alternatively, the enteric mass can be prepared by using a ready-made aqueous dispersion of the acid-insoluble polymer by adding alkaline materials such as ammonium, sodium, or potassium hydroxides or other alkalis that will cause the acid-insoluble polymer to dissolve. The plasticizer-wetted, film-forming polymer can then be mixed with the solution of the acid-insoluble polymer. The mass can also be prepared by dissolving the acid-insoluble polymer or polymers in the form of salts of the above-mentioned bases or alkalis directly in water and mixing the solution with the plasticizer-wetted, film-forming polymer. The mass is cast into films or ribbons using heat controlled drums or surfaces. The fill material is encapsulated in a soft capsule using a rotary die. The capsules are dried under controlled conditions of temperature and humidity. The final moisture content of the shell composition is from about 2% to about 10% by weight of the capsule shell, preferably from about 4% to about 8% by weight by weight of the capsule shell.

III. Methods of Use

Orlistat can be used for the control or prevention of obesity and hyperlipaemia. The dose of orlistat to be administered can be readily determined by the prescribing physician based on several factors, such as the age and weight of the patient. ALLI®, the over-the-counter formulation of orlistat, contains 60 mg of orlistat. XENICAL ORLISTAT®, which is prescription, contains 120 mg of orlistat. In one embodiment, the capsule contains a dose equivalent of 60 mg or 120 mg. In a preferred embodiment, the capsule contains a dose of 60 mg. The fill materials are encapsulated in convenient capsule sizes, making it easier for patients to swallow.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

EXAMPLES

Example 1

Preparation of a Liquid Fill Materials Containing Orlistat Dissolved in Medium Chain Triglycerides 14.039 grams of orlistat was added to 65.131 grams of Captex 355. The mixture was stirred with moderate heating, up to 40 to 45° C., for approximately one hour. A clear solution was obtained, having an orlistat concentration of 17.7%. The solution remained clear (i.e., showed no signs of precipitation of orlistat) at room temperature for eight weeks. The solution also remained stable under refrigeration (0 to −4° C.) over 30 days.

Alternatively, 0.189 grams of butylated hydroxyanisole was dissolved in 64.018 grams of Captex 355 with stirring. 14.41 grams of orlistat was added to the mixture. The mixture was stirred with moderate heating, up to 40 to 45° C., for approximately one hour. A clear solution was obtained, having an orlistat concentration of 18.1%. The solution remained clear (i.e., showed no signs of precipitation of orlistat) at room temperature for eight weeks. The solution also remained stable under refrigeration (0 to −4° C.) over 30 days.

Example 2

Preparation of a Fill Material Containing Orlistat Dissolved in Triethyl Citrate 0.127 grams of butylated hydroxyanisole was dissolved in 43.763 grams of triethyl citrate (TEC) with stirring. 7.152 grams of orlistat was added to the mixture. The mixture was stirred with moderate heating, up to 40 to 45° C., for approximately one hour. A clear solution was obtained, having an orlistat concentration of 14.1%. The solution remained clear (i.e., showed no signs of precipitation of orlistat) at room temperature for eight weeks. The solution also remained stable under refrigeration (0 to −4° C.) over 30 days.

Example 3

Stress Studies of Orlistat Solutions Prepared from Various Vehicles

Captex 355 solutions of orlistat, with or without butylated hydroxyanisole (BHA), prepared as described in Example 1, were divided into portions of about 5 grams, which were added to 20 ml glass scintillation vials with proper closure. The vials were put into an oven set at 65° C. and heated for 3 and 7 days, respectively. For comparison, orlistat powder was heated under the same conditions. Orlistat solutions in PEG 400, with or without BHA, having an orlistat concentration of about 10% (Example 7), were also heated under the same conditions. The samples were analyzed for assay value by HPLC, using a procedure adapted from the online published USP version. The results of the stress studies are shown in FIG. 1A. Orlistat was dissolved in polyethylene glycol (9.8% and 10.6% in the presence of 0.25% BHA) or Captex 355 (17.7% and 18.1% in the presence of 0.25% BHA). As shown in FIG. 1A, orlistat alone (◇) or dissolved in polyethylene glycol (□) in combination with an antioxidant (Δ) or a surfactant (○) exhibited severe degradation; only approximately 30-50% of the orlistat remained intact (i.e., did not degrade) over a period of 7 days. However, orlistat dissolved in Captex 355, alone (♦) or with the anti-oxidant butylated hydroxyanisole (BHA) (●) showed little or no degradation over a period of 7 days at 65° C.

Figure 1B:
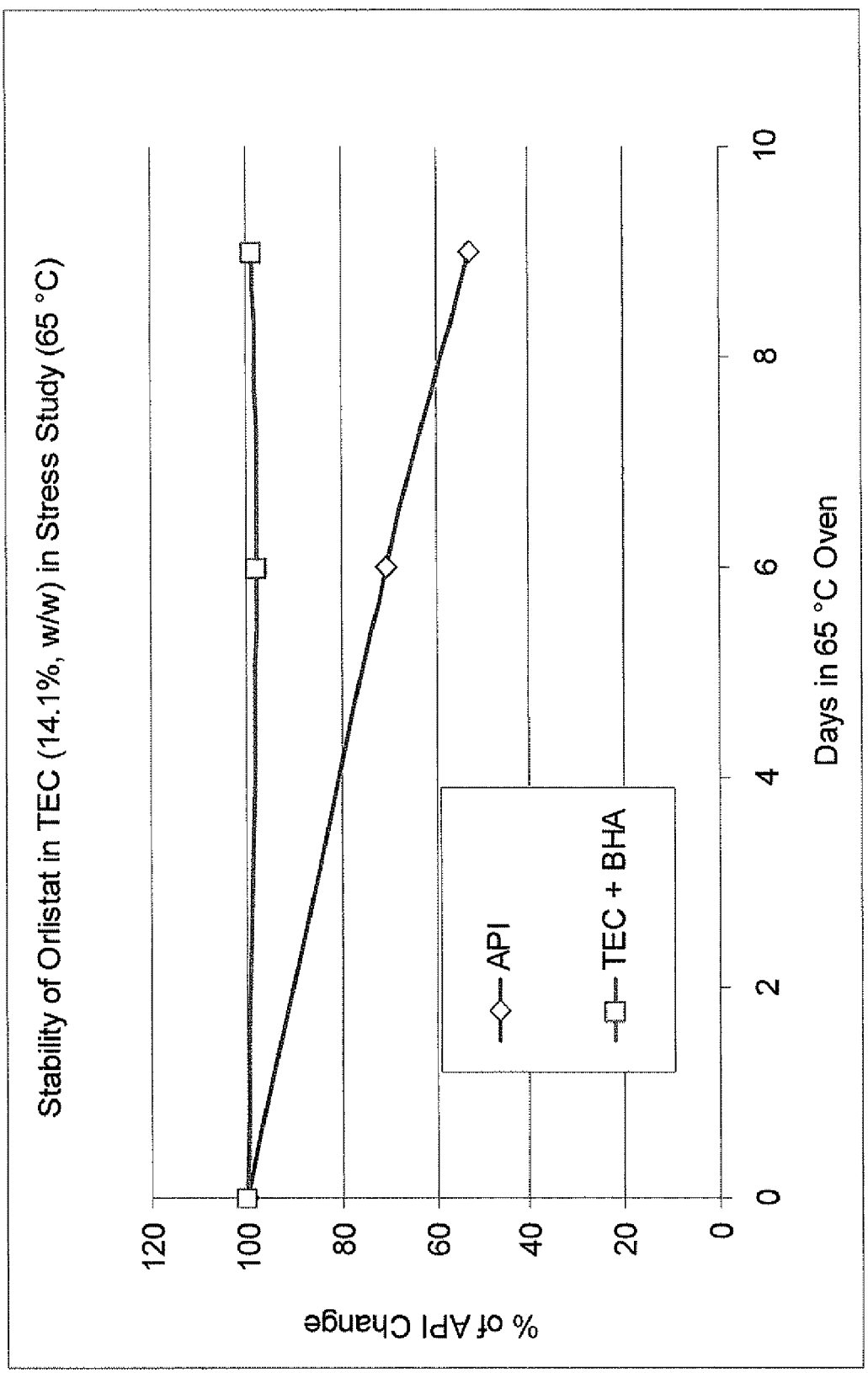

The stress study for the TEC solution was performed as described above for the Captex 355 solutions. The results are shown in FIG. 1B. FIG. 1B shows that orlistat dissolved in triethylcitrate, alone (□) or in combination with BHA (Δ), showed little or no degradation over a period of 9 days at 65° C.

Example 4

Encapsulation of Orlistat Solutions in a Two Piece Hard Gelatin Capsules and Softgel Capsules Hard Capsules
Captex 355 Solutions
Orlistat dissolved in Captex 355 (17.73%, w/w) was prepared as described in Example 1 and added to empty hard gelatin capsule (Size Number 1, made by Lilly and Company, Indianapolis, Ind.). Three capsules were filled. Each capsules contained 0.472 grams of the fill.

Triethylcitrate Solutions
Orlistat (5.055 grams) was dissolved in triethylcitrate (TEC, 14.956 grams). The concentration of orlistat was 25% w/w. The solution was added to empty hard gelatin capsule (Size Number 1). Three capsules were filled, with the total weight of fill being 1.387 grams. Each capsule contained 0.462 grams fill.

Softgel Capsules
Fill Formula A: Orlistat (72.005 grams) was dissolved in 528.396 grams of Captex 355 with stirring and mild heating (~37.5° C.). The concentration of orlistat was 12%.

Fill Formula B: Butylated hydroxyanisole (0.661 grams) was dissolved in 527.498 grams of Captex 355 with stirring and mild heating (~37.5° C.). Orlistat (72.002 grams) was added to the solution. Heating and mixing were continued until all the powder dissolved. The concentration of orlistat was ~12%. The concentration of BHA was 0.11%.

Fill Formula C: TEC (215.341 grams) was mixed with dl-tocopherol to form a homogeneous solution. Orlistat (72.962 grams) was added with stirring. The concentration of orlistat was 25%.

Preparation of gelatin: Bovine gelatin, extracted from bones, was mixed with appropriate amount of glycerin and water. The mixture was heated to 70° C. under continuous mixing for 24 hours, before cooling down to about 60° C. The gelatin mixture was added to the containers of an in-house assembled encapsulation machine. The ribbon thickness was maintained at 0.030 inches.

For the Captex 355 solution, the die size was 12 Oval, with the fill weight being 500 mg and containing 60 mg of orlistat.

For the TEC solution, the die size was 6 Oval, with the fill weight being 240 mg and containing 60 mg of orlistat.

The soft gel capsules containing fills A, B, and C were dried for 6 days.

Dissolution tests, assays, and stability tests were carried out. Capsules made from Captex 355 or TEC were stored at room temperature for up to 8 months and ten days (for Captex 355) and four months and 15 days (for TEC). The capsules were cut open and the fill materials observed visually. No precipitate or insoluble materials were observed in either of the formulations over the time periods described.

Figure 2:
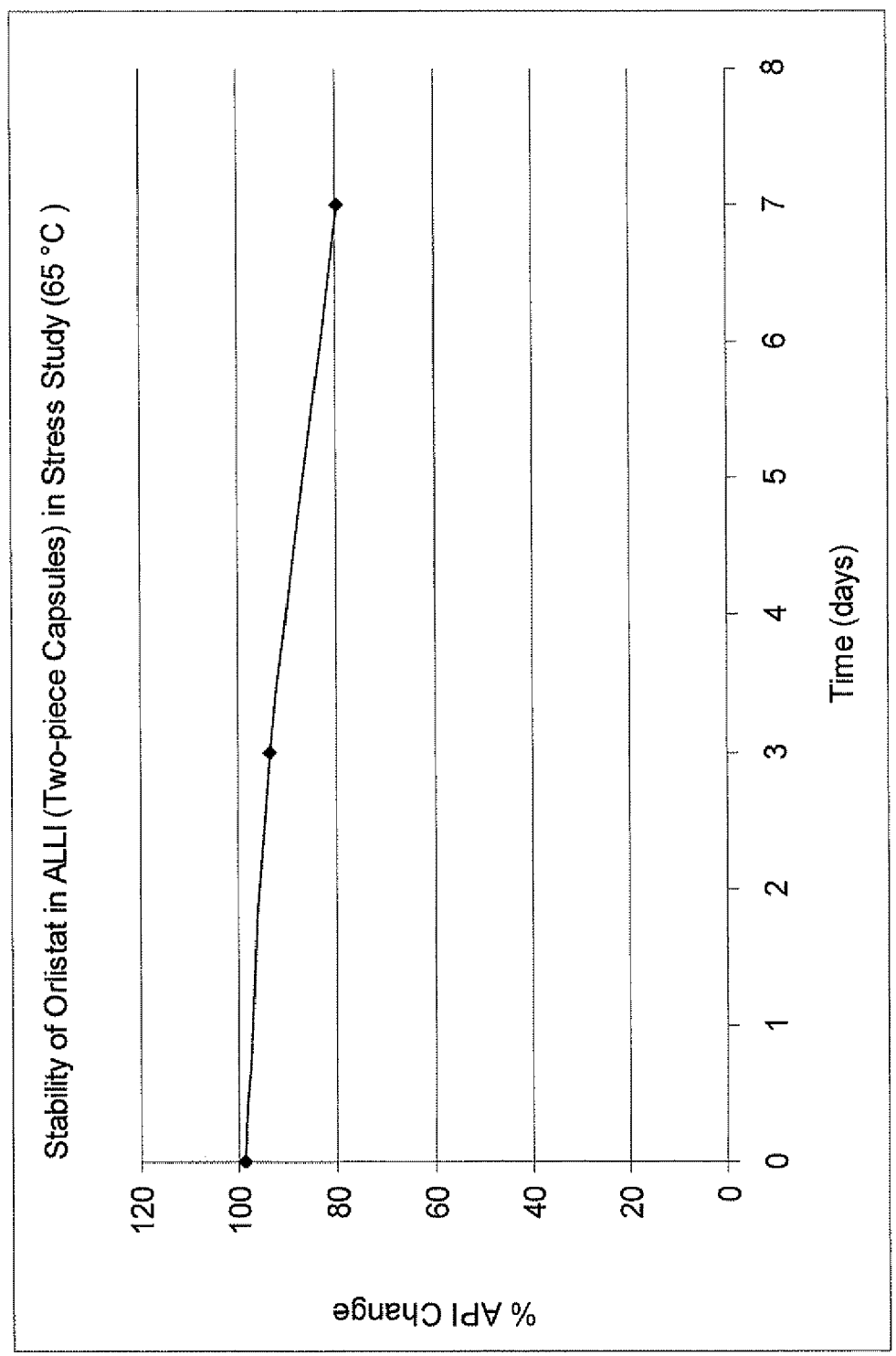
FIG. 2 is a graph showing percent degradation of the orlistat in ALLI® as a function of time (days) at 65° C.

The results of the stress study for ALLI® two piece hard gelatin capsules is shown in FIG. 2. In contrast to the capsules containing liquid fills prepared from Captex 355 and TEC, the orlistat in ALLI® degraded approximately 20% after seven days at 65° C.

Example 5

In Vitro Release Studies of Orlistat-Containing Captex 355 and Triethylcitrate Softgel Capsules Dissolution studies were performed using USP Dissolution Apparatus I (basket) or II (paddle) by changing the rotation speed and volume of the medium. The dissolution medium contained 3% of sodium dodecyl sulfate, 0.05% NaCl and 1 drop of Octyl Alcohol and the pH was adjusted to 6.0±0.20 with phosphoric acid (if necessary). Volumes of the dissolution medium were 900 mL, with rotation speeds varying from 75 to 150 rpm. All dissolution experiments were carried out at 37° C., for 45 min with aliquots of samples being taken every 15 min. The assay was carried out using an appropriate HPLC method run on an Agilent ChemStation.

Figure 3A:
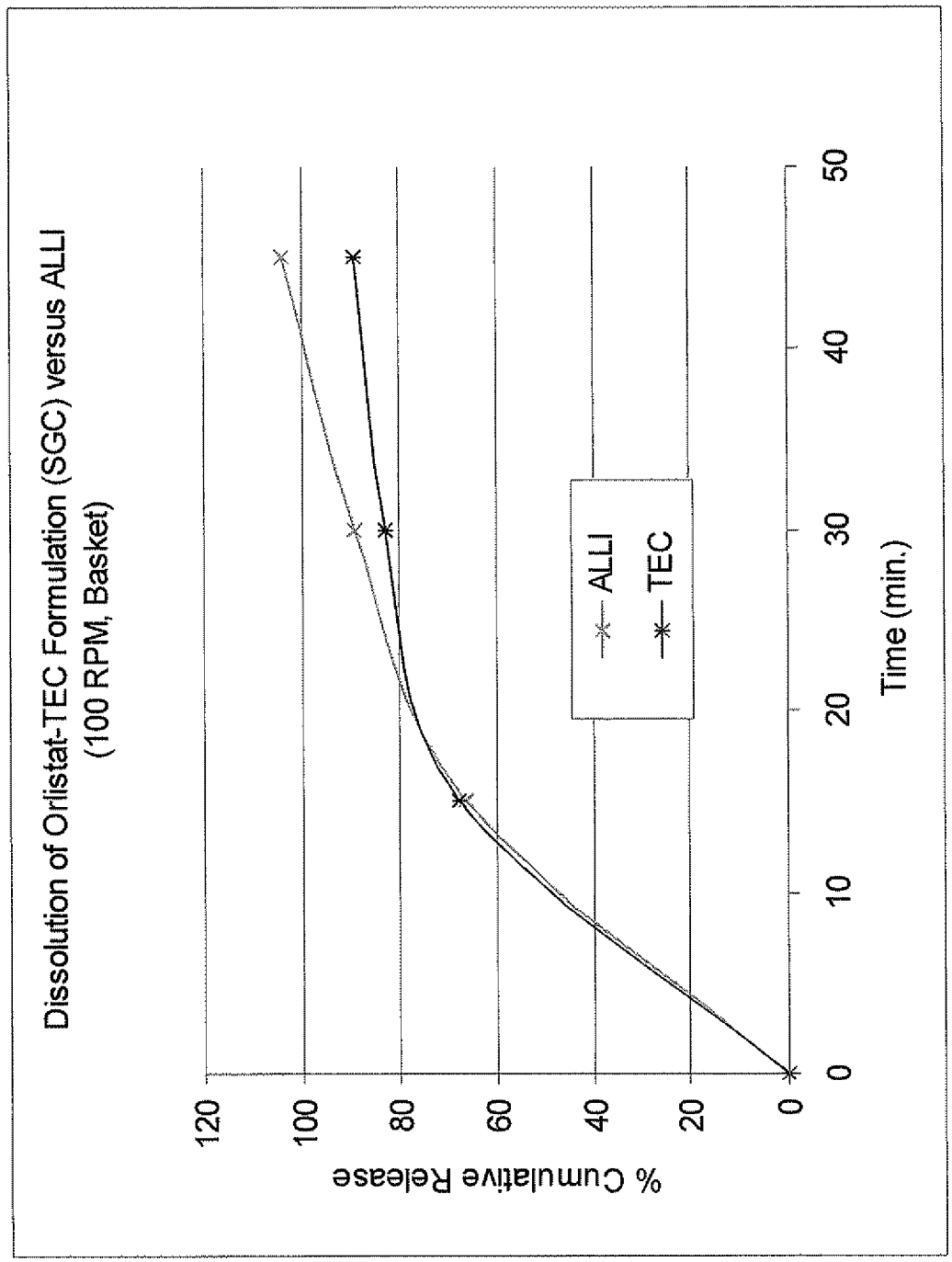
FIG. 3A is a graph comparing the percent cumulative release in vitro of orlistat from ALLI® and a soft gelatin capsule containing orlistat dissolved in triethyl citrate as a function of time (minutes).
Figure 3B:
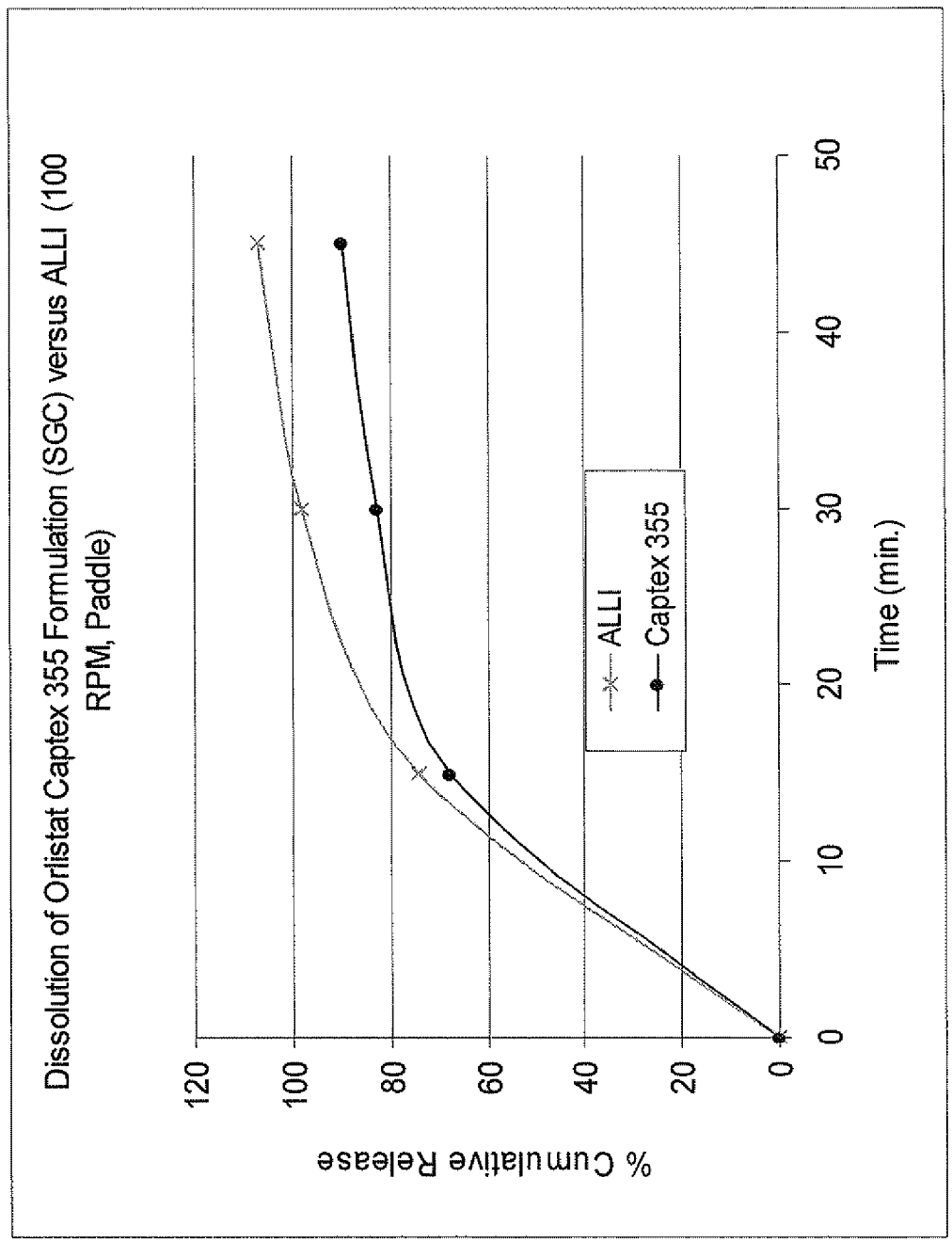
FIG. 3B is a graph comparing the percent cumulative release of orlistat from ALLI® (*) and a soft gelatin capsule containing orlistat dissolved in Captex 355 (●) as a function of time (minutes).

The results of the in vitro release studies are shown in FIG. 3. The commercially available orlistat formulation ALLI®, which contains granulated orlistat encapsulated in a hard shell capsule, released 100% of the orlistat over approximately 45 minutes (see FIGS. 3A and 3B). Orlistat dissolved in triethyl citrate (see FIG. 3A) or Captex 355 (see FIG. 3B) and encapsulated in a softgel capsule released approximately 90% of the orlistat over the same period of time. The USP (in process) specification for ALLI® in vitro dissolution is Q≧70% after 45 minutes at 75 rpm (paddle). The in vitro release studies described in FIG. 3 were conducted at 100 rpm (paddle or basket).

Example 6

In Vitro Release Studies of Orlistat-Containing Captex 355 and Triethylcitrate Two Piece Hard Shell Capsules Dissolution studies were performed using USP Dissolution Apparatus I (basket) or II (paddle) by changing the rotation speed, and volume of the medium. The dissolution medium contained 3% of sodium dodecyl sulfate, 0.05% NaCl and 1 drop of Octyl Alcohol. The pH of the dissolution medium was adjusted to 6.0±0.20 with phosphoric acid (if necessary).

The volume of the dissolution medium was either 500 or 900 mL, with rotation speeds varying from 75 to 150 rpm. All dissolution experiments were carried out at 37° C., for 45 min with aliquots of samples being taken every 15 min. The assay was carried out with an appropriate HPLC method being run on an Agilent ChemStation.

Figure 4:
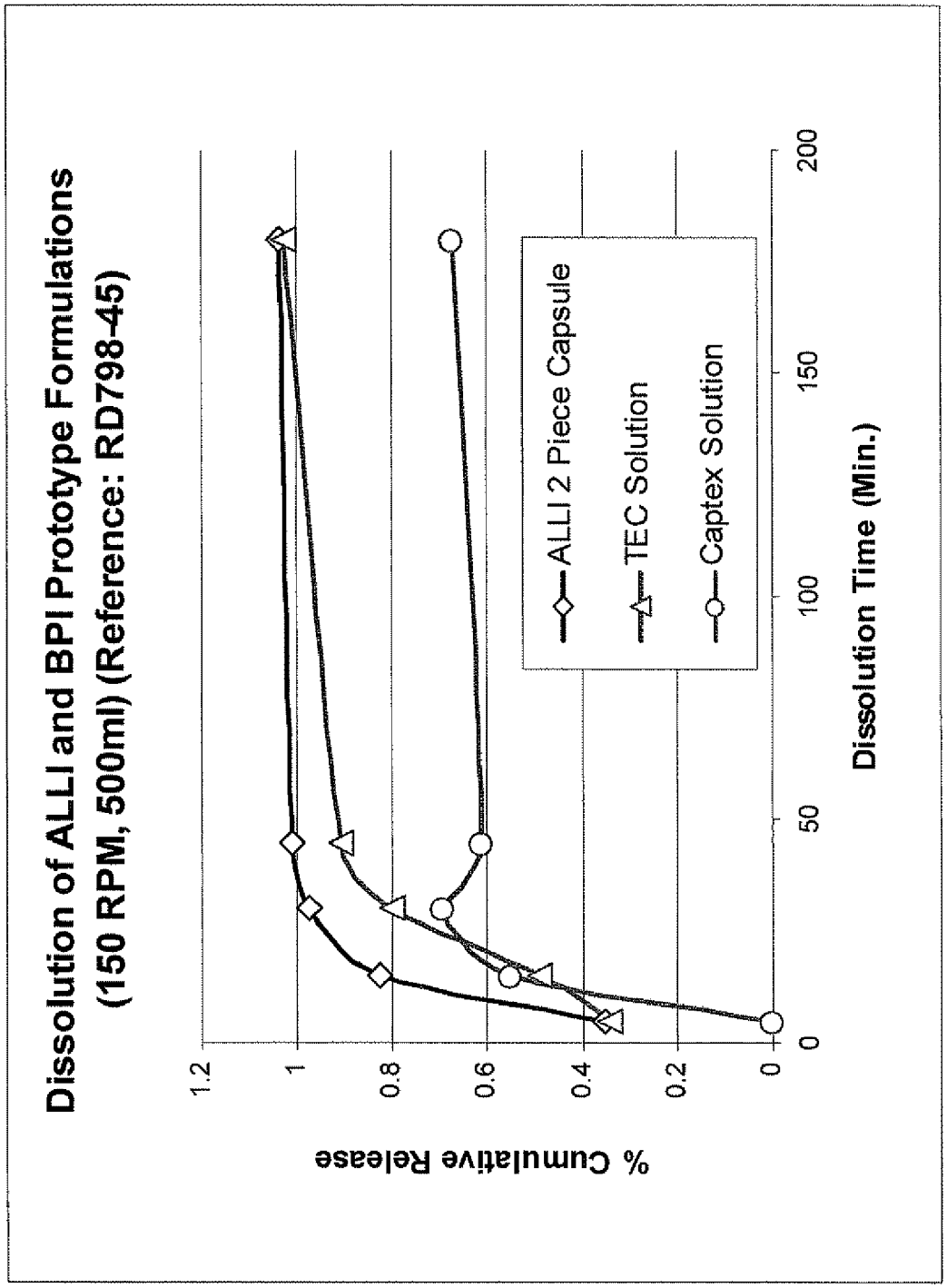
FIG. 4 is a graph showing the percent cumulative release in vitro of orlistat from ALLI® (◇) and two-piece hard shell capsules containing orlistat dissolved in triethyl citrate (△) and Captex 355 (○) as a function of time (minutes).

The results of the dissolution study are shown in FIG. 4. As shown in FIG. 4, the TEC formulation released its content faster than the Captex formulation. In the latter formulation, more than 60% of the content was released at 45 min.

Example 7

Preparation of a Fill Material Containing Orlistat Dissolved in Polyethylene Glycol 7.041 grams of orlistat was added to 64.979 grams of PEG 400. The mixture was stirred with moderate heating, up to 40 to 45° C., for approximately six hours. A clear solution was obtained, having an orlistat concentration of 9.78%. The solution solidified to become waxy when cooled to room temperature or below. Upon heating to 40 to 45° C. for a few hours, the waxy material became clear liquid, which again became waxy (solidified) upon cooling.

In another example, 0.186 grams of butylated hydroxyanisole (BHA) was dissolved in 65.075 grams of PEG 400 with stirring under moderate heating. 7.746 grams of orlistat was added to the mixture. The mixture was stirred under moderate heating, up to 40 to 45° C., for approximately six hours. A clear solution was obtained, having an orlistat concentration of 10.6%. The solution solidified to become waxy when cooled to room temperature or below. Upon heating to 40 to 45° C. for a few hours, the waxy material became a clear liquid, which became waxy upon cooling.

In another example, 1.854 grams of orlistat was added to 19.945 grams of PEG 600. The mixture was stirred with moderate heating, up to 40 to 45° C., for approximately six hours. A clear solution was obtained, having an orlistat concentration of 8.5%. The solution solidified to become waxy when cooled to room temperature or below. Upon heating to 40 to 45° C. for a few hours, the waxy material became a clear liquid, which became waxy upon cooling.

The PEG solutions of orlistat solidify upon cooling to room temperature resulting in soft capsules that are not clear and transparent. Further, as shown in FIG. 1a, orlistat is incompatible with PEG. PEG solutions of orlistat lost approximately 30% of the orlistat when heated for 7 days at 65° C. In contrast, solutions of orlistat in Captex 355 or TEC (FIGS. 1a and 1b), retained more than 90% of the active agent.

We claim:

1. A soft or hard capsule comprising a liquid fill material comprising orlistat and a pharmaceutically acceptable carrier, wherein the carrier is selected from the group consisting of one or more medium chain triglycerides or partial triglycerides which are liquids at about −5° C., one or more $C_1$-$C_{10}$ esters of citric acid, and combinations thereof.

2. The capsule of claim 1, wherein the one or more medium chain triglycerides or partial triglycerides comprise $C_2$-$C_{12}$ alkyl chains.

3. The capsule of claim 2, wherein the one or more medium chain triglycerides or partial triglycerides comprise $C_8$-$C_{10}$ alkyl chains.

4. The capsule of claim 2, wherein the one or more medium chain triglycerides or partial triglycerides are selected from the group consisting of caprylic and capric triglycerides, and combinations thereof.

5. The capsule of claim 4, wherein the medium chain triglyceride is a caprylic and capric triglyceride.

6. The capsule of claim 1, wherein the one or more $C_1$-$C_{10}$ esters of citric acid are selected from the group consisting of triethylcitrate, acetyltributyl citrate, acetyltriethyl citrate, tributyl citrate, and combinations thereof.

7. The capsule of claim 1, wherein the fill material is substantially free of surfactant.

8. The capsule of claim 1, wherein the fill material further comprises an antioxidant.

9. The capsule of claim 8, wherein the antioxidant is selected from the group consisting of butylated hydroxyanisole (BHA); ascorbic acid, its salts and esters; Vitamin E, tocopherol and its salts; sodium metabisulphite; propyl gallate; and butylated hydroxytoluene (BHT).

10. The capsule of claim 1, wherein the percent loading of orlistat is from about 5% to about 45% by weight of the fill material.

11. The capsule of claim 10, wherein the percent loading of orlistat is from about 5% to about 30% by weight of the fill material.

12. The capsule of claim 10, wherein the percent loading of orlistat is from about 5% to about 20% by weight of the fill material.

13. The capsule of claim 1, wherein the percent degradation of orlistat is less than 10% when the capsule is heated at 65° C. for 7 days.

14. The capsule of claim 13, wherein the percent degradation of orlistat is less than 5% when the capsule is heated at 65° C. for 7 days.

15. The capsule of claim 13, wherein the percent degradation of orlistat is less than 1% when the capsule is heated at 65° C. for 7 days.

16. The capsule of claim 1, wherein the capsule is a soft capsule.

17. The capsule of claim 16, wherein the capsule is a soft gelatin capsule.

18. The capsule of claim 17, wherein the soft gelatin capsule is an enteric capsule containing an acid insoluble polymer in the capsule shell.

19. The capsule of claim 1, wherein the capsule is a hard capsule.

20. The capsule of claim 19, wherein the capsule is a hard gelatin capsule.

21. A method of making the capsule of claim 1, comprising dissolving orlistat in the carrier to form a solution and encapsulating the solution in a soft or hard capsule.

22. A method for treating obesity comprising administering to a subject in need thereof the capsule of claim 1.

23. The capsule of claim 7, wherein the fill material contains less than 0.1% surfactant.

24. The capsule of claim 7, wherein the fill materials contains no surfactant.

* * * * *